United States Patent
Tojo et al.

(10) Patent No.: US 10,307,211 B2
(45) Date of Patent: Jun. 4, 2019

(54) MULTIPOINT DETECTION FIBER SENSOR AND INSERTION APPARATUS INCLUDING MULTIPOINT DETECTION FIBER SENSOR

(71) Applicant: OLYMPUS CORPORATION, Tokyo (JP)

(72) Inventors: Ryo Tojo, Hachioji (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/331,200

(22) Filed: Oct. 21, 2016

(65) Prior Publication Data

US 2017/0035516 A1    Feb. 9, 2017

Related U.S. Application Data

(63) Continuation of application No. PCT/JP2015/064611, filed on May 21, 2015.

(30) Foreign Application Priority Data

May 29, 2014    (JP) ................. 2014-111698

(51) Int. Cl.
*G02B 23/26* (2006.01)
*G01B 11/24* (2006.01)
(Continued)

(52) U.S. Cl.
CPC .............. *A61B 34/20* (2016.02); *A61B 1/005* (2013.01); *A61B 1/0017* (2013.01);
(Continued)

(58) Field of Classification Search
CPC ....... A61B 34/20; A61B 5/065; A61B 1/00167; A61B 1/00045; A61B 1/0017;
(Continued)

(56) References Cited

U.S. PATENT DOCUMENTS

2007/0116415 A1    5/2007  Kobayashi
2014/0036261 A1    2/2014  Fujita et al.

FOREIGN PATENT DOCUMENTS

JP    2002355215 A    12/2002
JP    2003-052614 A    2/2003
(Continued)

OTHER PUBLICATIONS

English machine translation of JP2003075133.*
(Continued)

*Primary Examiner* — John Bedtelyon
(74) *Attorney, Agent, or Firm* — Scully, Scott, Murphy & Presser, P.C.

(57) ABSTRACT

A multipoint detection fiber sensor including a plurality of sensing parts at a plurality of positions is provided. The sensing parts are able to detect curve amounts respectively. The multipoint detection fiber sensor includes a plurality of optical fibers arranged in an overall effective detection area that is an extent in which the multipoint detection fiber sensor detects curve amounts. Each of the optical fibers includes the plurality of sensing parts. The multipoint detection fiber sensor also includes a light source which supplies light to the optical fibers and a light receiver which receives light emitted through the optical fibers to which light is supplied. Furthermore, an insertion apparatus into which the multipoint detection fiber sensor is incorporated is provided.

17 Claims, 19 Drawing Sheets

(51) Int. Cl.
*G02B 23/24* (2006.01)
*G01N 21/31* (2006.01)
*A61B 34/20* (2016.01)
*A61B 1/00* (2006.01)
*A61B 5/06* (2006.01)
*A61B 1/005* (2006.01)

(52) U.S. Cl.
CPC ...... *A61B 1/00045* (2013.01); *A61B 1/00167* (2013.01); *A61B 5/065* (2013.01); *G01B 11/24* (2013.01); *G01N 21/31* (2013.01); *G02B 23/2476* (2013.01); *A61B 2034/2061* (2016.02); *A61B 2562/0266* (2013.01); *A61B 2562/043* (2013.01); *G01N 2201/088* (2013.01); *G02B 23/26* (2013.01)

(58) Field of Classification Search
CPC ............ A61B 1/005; A61B 2562/0266; A61B 2562/043; A61B 2034/2061; G02B 23/2476; G02B 23/26; G01B 11/24; G01N 21/31; G01N 2201/088
See application file for complete search history.

(56) References Cited

FOREIGN PATENT DOCUMENTS

| JP | 2003075133 A | 3/2003 |
|---|---|---|
| JP | 2003-225195 A | 8/2003 |
| JP | 2007-143600 A | 6/2007 |
| JP | 2010-107239 A | 5/2010 |
| JP | 2012-220241 A | 11/2012 |

OTHER PUBLICATIONS

International Search Report dated Jul. 21, 2015 issued in PCT/JP2015/064611.
Chinese Office Action dated Jul. 26, 2017 in Chinese Patent Application No. 201580028388.9.
German Search Report dated Oct. 30, 2017 in German Patent Application No. 11 2015 002 535.9.
German Office Action dated Oct. 31, 2017 in German Patent Application No. 11 2015 002 535.9.
Japanese Office Action dated Oct. 10, 2017 in Japanese Patent Application No. 2014-111698.
English translation of International Preliminary Report on Patentability dated Dec. 8, 2016 together with the Written Opinion received in related International Application No. PCT/JP2015/064611.
Japanese Office Action dated Jul. 24, 2018 in Japanese Patent Application No. 2014-111698.
Japanese Office Action dated May 15, 2018 in Japanese Patent Application No. 2014-111698.
Chinese Office Action dated Jun. 12, 2018 in Chinese Patent Application No. 201580028388.9.

* cited by examiner

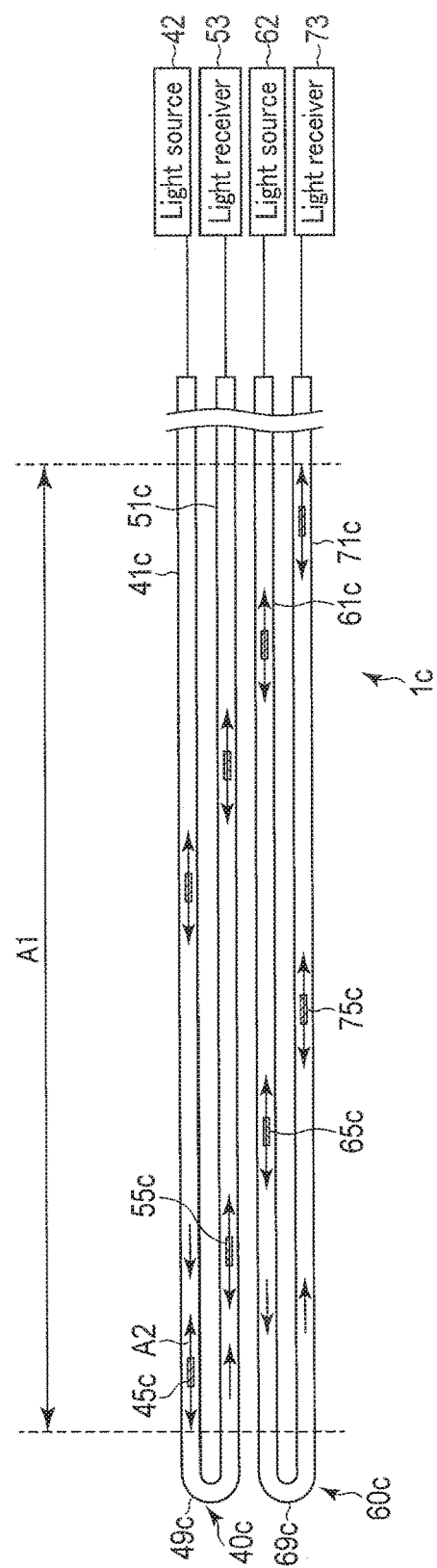
F I G. 9

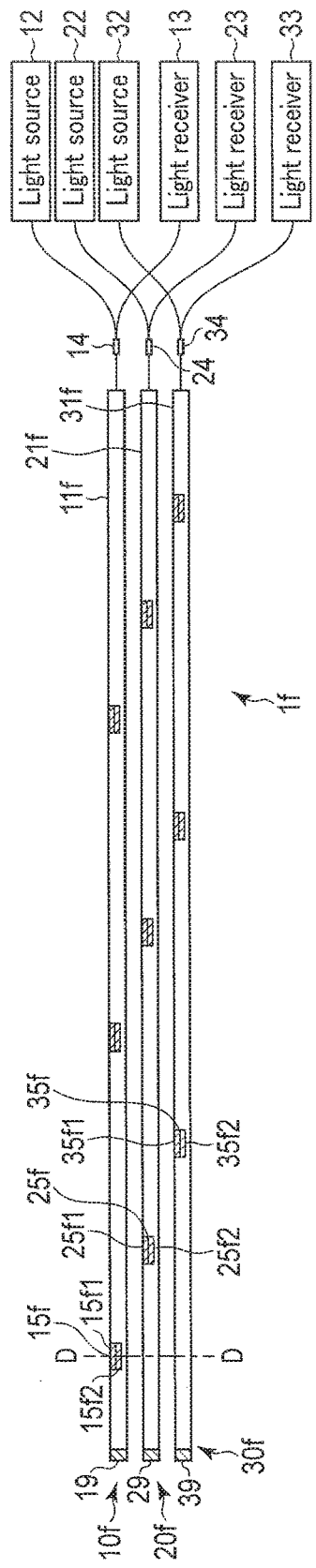
F I G. 12

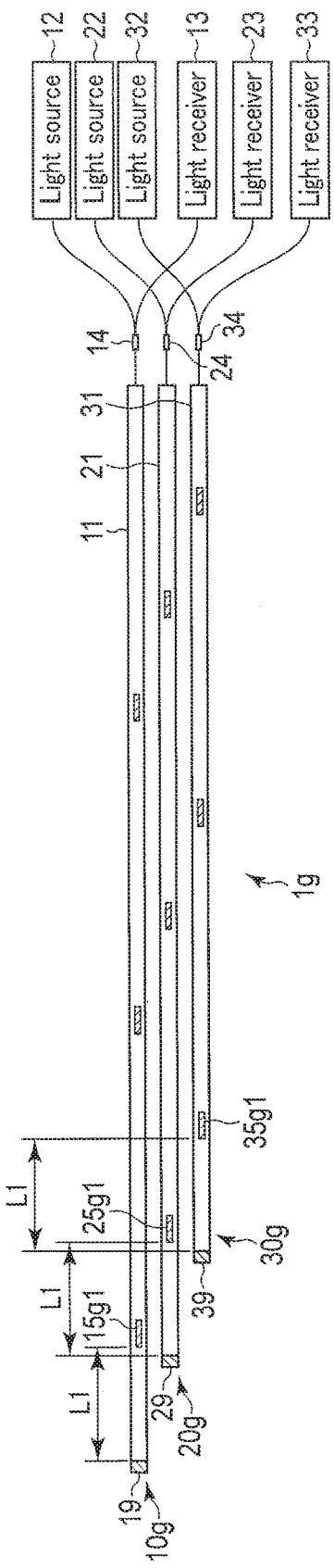
F I G. 14

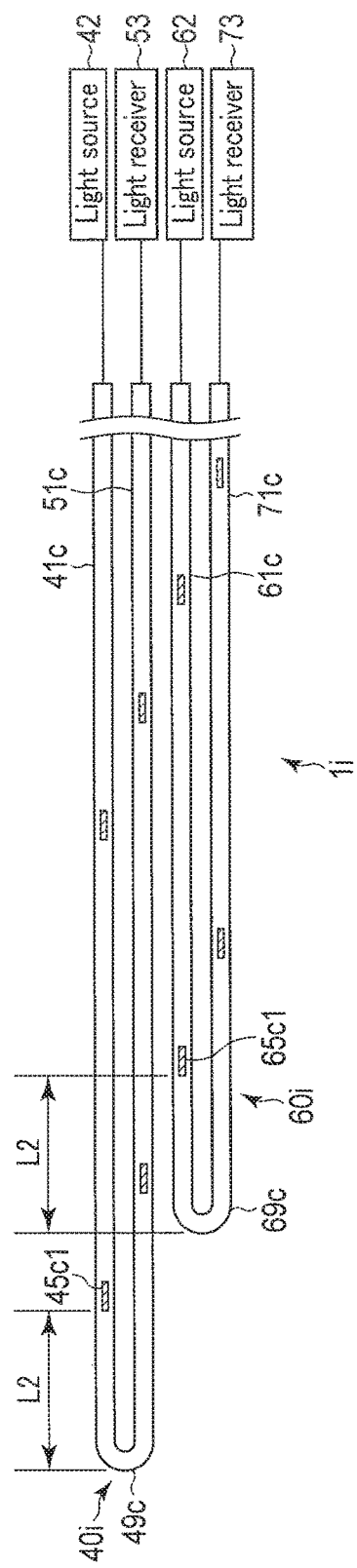
F I G. 16

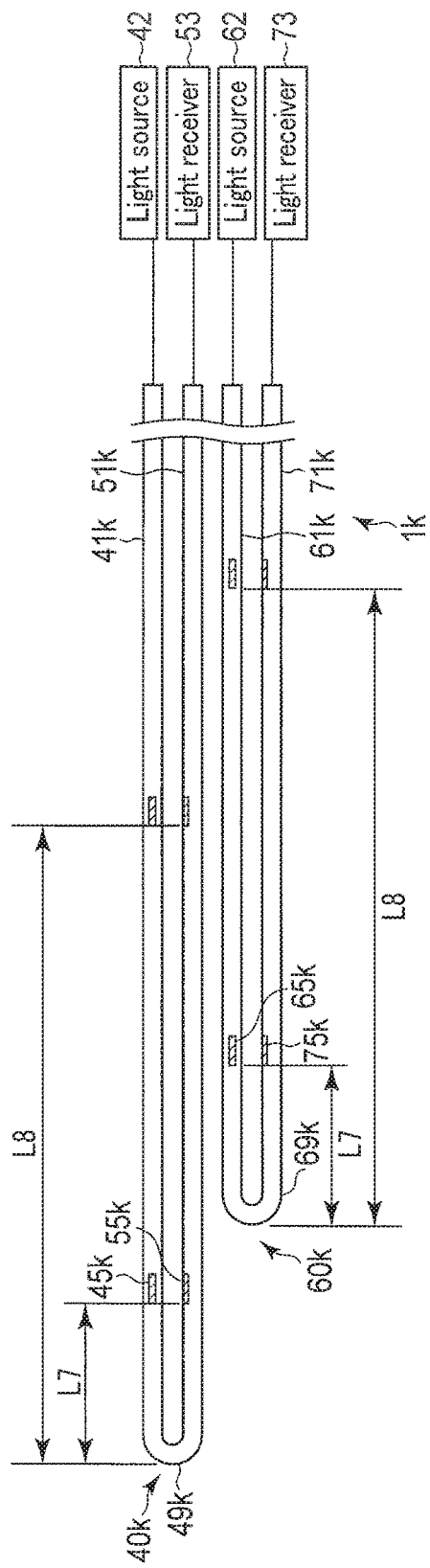
F I G. 18

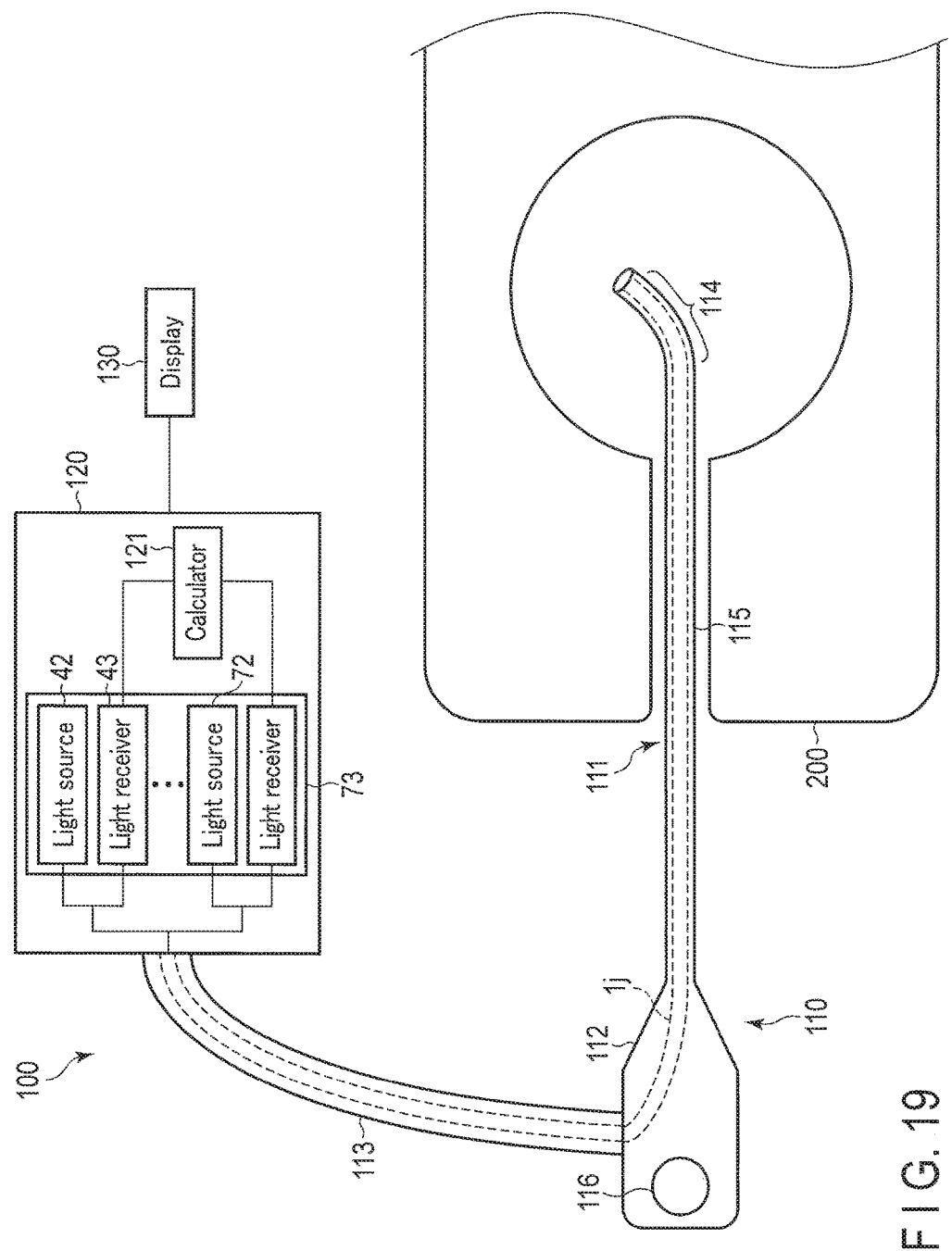
F I G. 19

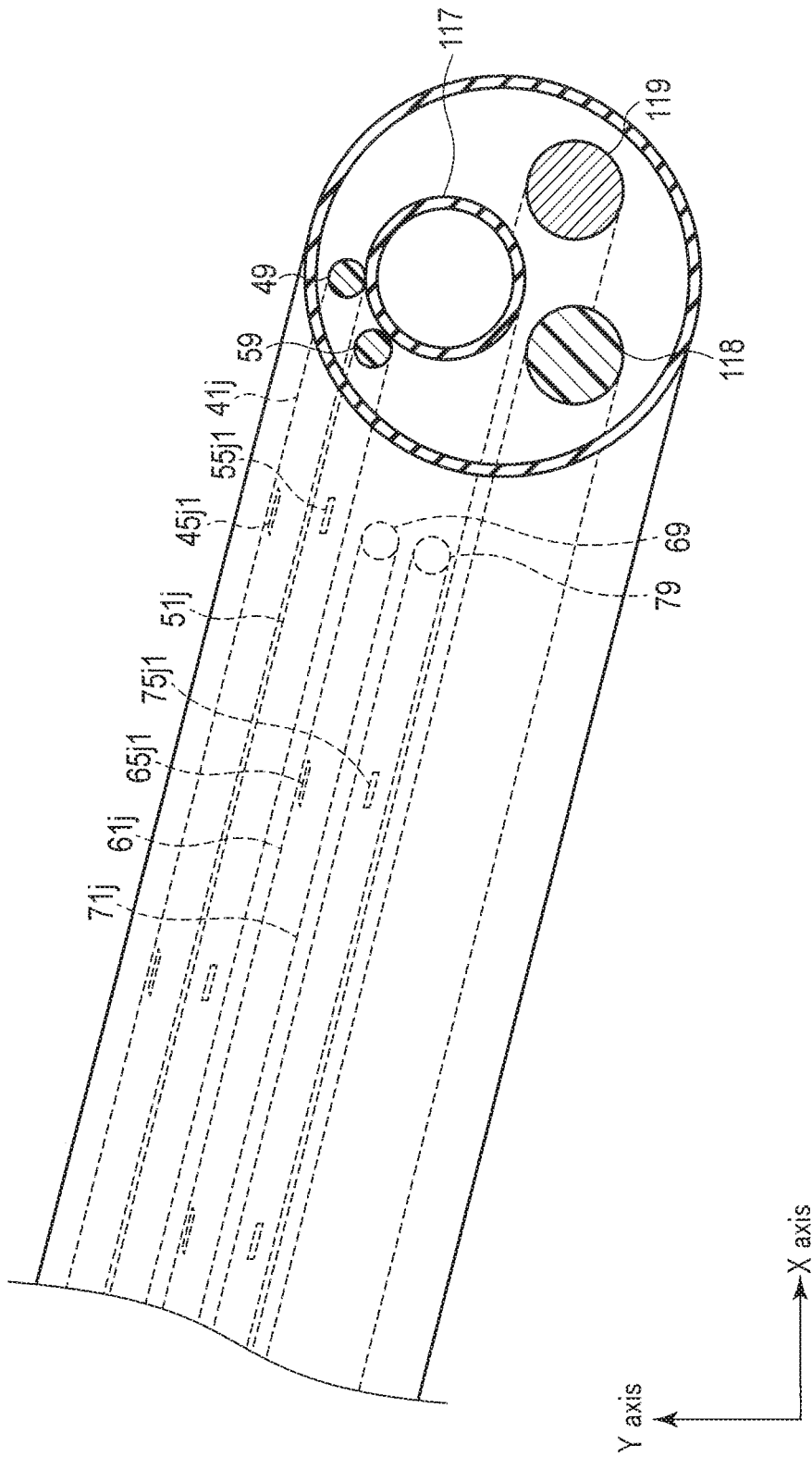
F I G. 20

MULTIPOINT DETECTION FIBER SENSOR AND INSERTION APPARATUS INCLUDING MULTIPOINT DETECTION FIBER SENSOR

CROSS-REFERENCE TO RELATED APPLICATIONS

This application is a Continuation Application of PCT Application No. PCT/JP2015/064611, filed May 21, 2015 and based upon and claiming the benefit of priority from prior the Japanese Patent Application No. 2014-111698, filed May 29, 2014, the entire contents of all of which are incorporated herein by references.

BACKGROUND OF THE INVENTION

1. Field of the Invention

The present invention relates to a multipoint detection fiber sensor and an insertion apparatus including the multipoint detection fiber sensor.

2. Description of the Related Art

A curved-shape detection sensor (fiber sensor) used together with an insertion apparatus including a flexible insertion section is known. Such a fiber sensor is incorporated into the insertion section in the insertion apparatus and curved integrally with the insertion section to detect a curved shape thereof.

For example, Jpn. Pat. Appln. KOKAI Publication No. 2003-52614 discloses an endoscope apparatus to which a fiber sensor as described above is attached. The fiber sensor includes a plurality of optical fibers, and each optical fiber is provided with a sensing part to cause a transmission amount of light to be varied corresponding to the angle at which the fiber is curved. The optical fibers are arranged in parallel with and attached to a flexible band-shaped member, and the band-shaped member is inserted through an insertion section of an endoscope almost throughout its length. In the endoscope apparatus, a curved shape of the band-shaped member at a position of each sensing part is detected from the transmission amount of light of each optical fiber, and the curved shape is displayed on a monitor screen as a curved shape of the insertion section.

BRIEF SUMMARY OF THE INVENTION

One embodiment of the invention is a multipoint detection fiber sensor including a plurality of sensing parts at a plurality of positions, the sensing parts being able to detect curve amounts respectively, the multipoint detection fiber sensor comprising a plurality of optical fibers arranged in an overall effective detection area that is an extent in which the multipoint detection fiber sensor detects curve amounts, each of the optical fibers including a plurality of sensing parts, a light source which supplies light to the optical fibers, and a light receiver which receives light emitted through the optical fibers to which light is supplied.

Furthermore, another embodiment of the invention is an insertion apparatus comprising a flexible insertion section inserted into an insertion target, a plurality of sensing parts at a plurality of positions of the insertion section, the sensing parts being able to detect curve amounts respectively, the sensing parts being incorporated into a plurality of optical fibers arranged in an overall effective detection area that is a range in which the sensing parts detect curve amounts, each of the optical fibers including the sensing parts, a light source that supplies light to the optical fibers, and a light receiver that receives light emitted through the optical fibers to which light is supplied.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 9 is a diagram showing the overall structure of a multipoint detection fiber sensor according to variant 1 of the first embodiment.

FIG. 12 is a diagram showing the overall structure of a multipoint detection fiber sensor according to variant 4 of the first embodiment.

FIG. 14 is a diagram showing the overall structure of a multipoint detection fiber sensor according to variant 5 of the first embodiment.

FIG. 16 is a diagram showing the overall structure of a multipoint detection fiber sensor according to variant 7 of the first embodiment.

FIG. 18 is a diagram showing the overall structure of a multipoint detection fiber sensor according to variant 9 of the first embodiment.

FIG. 19 is a diagram showing the overall structure of an insertion apparatus according to a second embodiment.

FIG. 20 is a diagram showing the internal structure of an insertion section.

DETAILED DESCRIPTION OF THE INVENTION

First Embodiment (Overview of Multipoint Detection Fiber Sensor)

Figure 1:
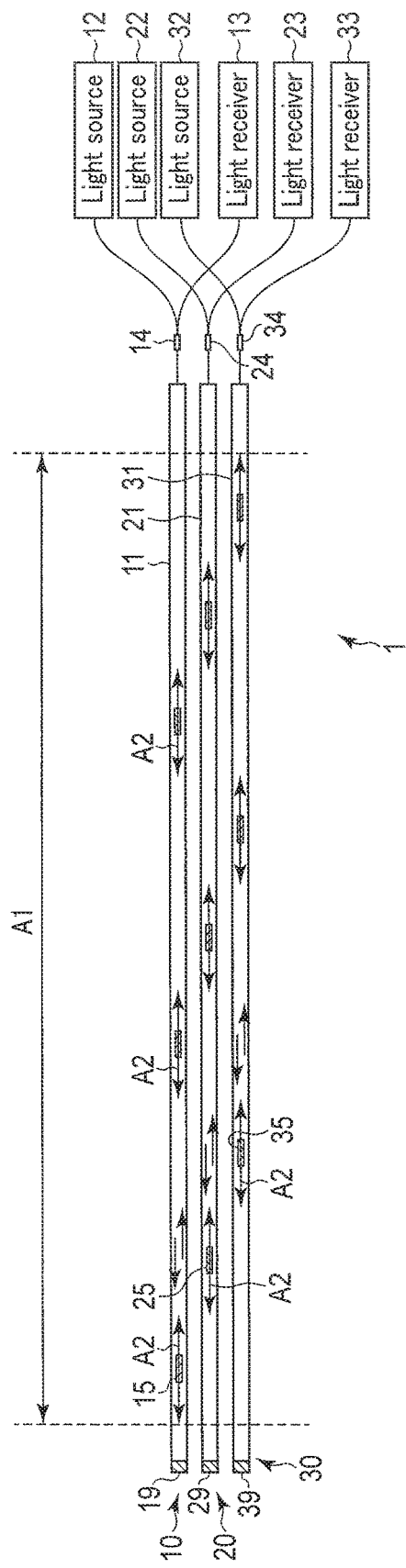
FIG. 1 is a diagram showing the overall structure of a multipoint detection fiber sensor according to a first embodiment.

FIG. 1 is a diagram showing the overall structure of a multipoint detection fiber sensor 1 according to a first embodiment. In the specification, the term "multipoint" is used to mean two or more points. The multipoint detection fiber sensor 1 includes a first sensor unit 10, a second sensor unit 20 and a third sensor unit 30.

The first sensor unit 10 includes a first optical fiber 11, a light source 12 that supplies light to the first optical fiber 11, a light receiver 13 that receives light emitted through the first optical fiber 11, and an optical coupler 14 that connects the first optical fiber 11 and the light source 12 and connects the first optical fiber 11 and the light receiver 13. Similarly, the second sensor unit 20 and the third sensor unit 30 respectively include a second optical fiber 21 and a third optical fiber 31, light sources 22 and 32 that supply light to the second and third optical fibers 21 and 31, light receivers 23 and 33 that receive light emitted through the second and third optical fibers 21 and 31, and optical couplers 24 and 34 that connect their respective optical fibers and light sources and connect their respective optical fibers and light receivers.

The first, second and third sensor units 10, 20 and 30 have the same structure, except for the arrangement of sensing parts 15, 25 and 35 described later. Hereinafter, the description of the structure of the first sensor unit 10 will be given, and the descriptions of the structures of the second and third sensor units 20 and 30 will be omitted.

(Light Source and Optical Coupler)

The light source 12 emits light containing wavelength components of a characteristic absorption bands described later. The light source 12 is optically connected to the proximal end of the first optical fiber 11 via the optical coupler 14. The light emitted from the light source 12 falls on the first optical fiber 11 through the optical coupler 14. The optical coupler 14 can be replaced with another element capable of splitting light, such as a beam splitter.

(Optical Fiber)

Figure 2:
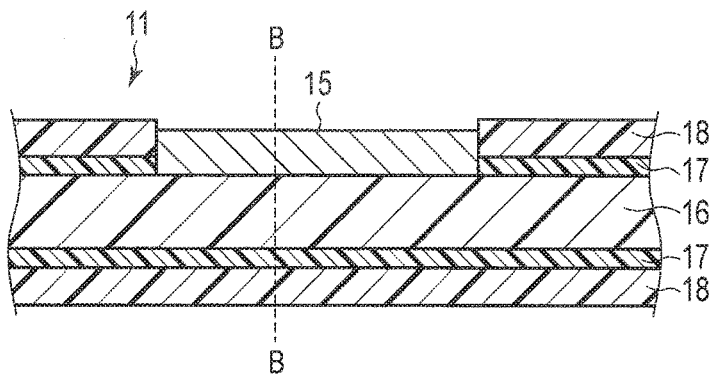
FIG. 2 is an enlarged sectional view of a first optical fiber, taken along the optical axis direction of the first optical fiber.
Figure 3:
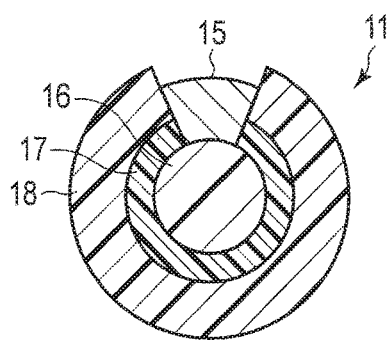
FIG. 3 is a sectional view, taken along the line B-B of FIG. 2.

FIG. 2 is an enlarged sectional view of the first optical fiber 11 (hereinafter referred to as optical fiber 11), taken along the optical axis direction (longitudinal direction) of the optical fiber. FIG. 3 is a sectional view, taken along the line B-B of FIG. 2. The optical fiber 11 includes a core 16, a cladding 17 surrounding the core 16, and a jacket 18 surrounding the cladding 17. In the optical fiber 11, a plurality of sensing parts 15 that respectively detect curve amounts are provided at different positions in the longitudinal direction. Since the optical fiber 11 includes a plurality of sensing parts 15, one optical fiber is able to detect curve amounts at a plurality of points.

The sensing parts 15 are formed by removing part of the jacket 18 and cladding 17 by, e.g. laser processing to expose the core 16 and providing an absorber on the exposed core 16 to cause a characteristic absorption band described later. The absorber is formed of, e.g. a member in which pigment is mixed with resin whose refractive index is lower than that of the core 16. Different pigments are used for the sensing parts 15 of the optical fiber 11.

The absorber of the sensing parts 15 absorbs part of light (light having a specific wavelength or a wavelength range) which passes through the sensing parts 15 by the absorption wavelength characteristics of the pigments. Light having the other wavelengths or wavelength ranges is reflected and guided through the core 16 because the resin of the absorber has a refractive index that is lower than that of the core 16.

Figure 4:
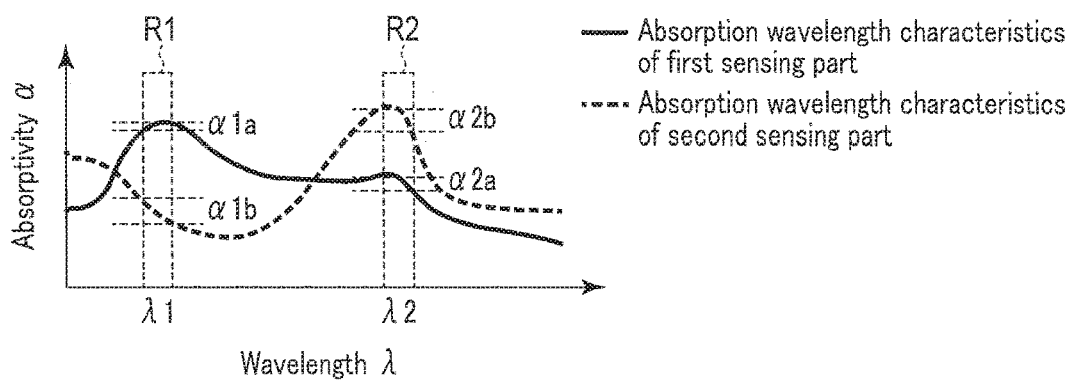
FIG. 4 is a graph showing absorption wavelength characteristics of sensing parts.

FIG. 4 is a graph showing the absorption wavelength characteristics of the sensing parts 15. In FIG. 4, one of the sensing parts 15, which is the nearest to the distal end of the optical fiber 11, is defined as a first sensing part, and its adjacent one is defined as a second sensing part. The first and second sensing parts include characteristic absorption bands. The characteristic absorption bands is a wavelength range of mutual absorption (that is, the wavelength range in which the first and second sensing parts have absorptivity) and a wavelength range of different absorption wavelength characteristics (that is, a wavelength range in which the first and second sensing parts differ in absorptivity from each other). The number of characteristic absorption bands is equal to or larger than that of sensing parts (that is, two or more characteristic absorption bands).

In FIG. 4, the two characteristic absorption bands are shown as a first characteristic absorption band R1 and a second characteristic absorption band R2. The first characteristic absorption band R1 is a band including wavelength $\lambda 1$, and a range of absorptivity $\alpha 1a$ of the first sensing part and a range of absorptivity $\alpha 1b$ of the second sensing part in the first characteristic absorption band R1 are different from each other. Furthermore, the second characteristic absorption band R2 is a band including wavelength $\lambda 2$, and a range of absorptivity $\alpha 2a$ of the first sensing part and a range of absorptivity $\alpha 2b$ of the second sensing part in the second characteristic absorption band R2 are different from each other. The characteristic absorption bands may be interpreted as a specific wavelength (e.g. $\lambda 1$ or $\lambda 2$) having no wavelength range. To make description simple, FIG. 4 shows two sensing parts; however, if the number of sensing parts is three or more, similar things can be applied.

Figure 5A:
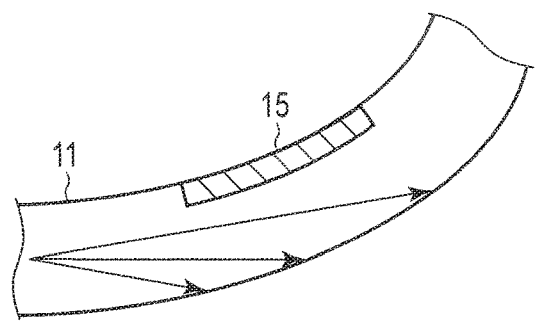
FIG. 5a is a schematic view of light guided near a sensing part with the sensing part curved inwardly.
Figure 5B:
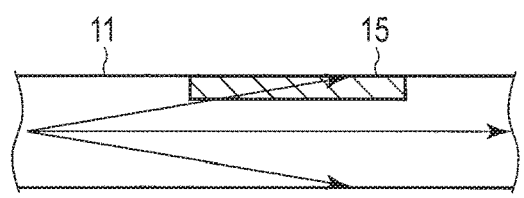
FIG. 5b is a schematic view of light guided near a sensing part with the sensing part straight.
Figure 5C:
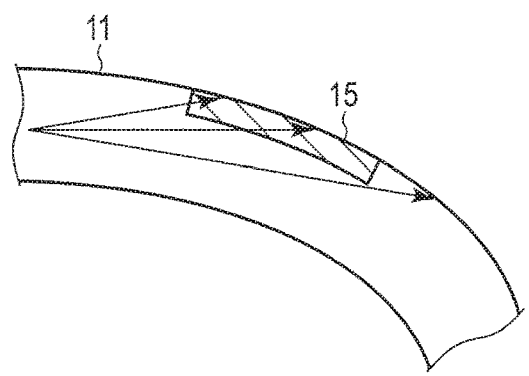
FIG. 5c is a schematic view of light guided near a sensing part with the sensing part curved outwardly.

FIGS. 5a to 5c are schematic views of light guided near a sensing part 15 of the optical fiber 11. When the optical fiber is straight, the sensing part 15 absorbs part of light guided through the optical fiber 11 as shown in FIG. 5b. When the optical fiber 11 is curved such that the sensing part 15 is located inwardly, light applied to the sensing part 15 decreases and thus the amount of light absorbed by the sensing part 15 becomes small (FIG. 5a). Accordingly, the transmission amount of light guided through the optical fiber 11 increases. On the other hand, when the optical fiber 11 is curved such that the sensing part 15 is located outwardly, light applied to the sensing part 15 increases and thus the amount of light absorbed by the sensing part 15 becomes large (FIG. 5c). Accordingly, the transmission amount of light guided through the optical fiber 11 decreases.

As described above, the amount of light transmitted to the sensing part 15, which is included in the light guided through the optical fiber 11, varies in accordance with the curve of the sensing part 15. In other words, the amount of light absorbed by the absorber of the sensing part 15 varies in the characteristic absorption bands. Then, a calculator, not shown, performs computation based on the amount of variation in light in a plurality of characteristic absorption bands to obtain an amount of curve of the sensing part 15. Incidentally, the relationship between the amount of curve and the amount of variation in light is acquired in advance by measurements.

One end of the optical fiber 11 that is different from another end thereof to which the optical coupler 14 is connected, or the distal end of the optical fiber 11 is provided with a return reflector 19. The return reflector 19 is formed by, e.g. evaporating aluminum onto the distal end of the optical fiber 11. The light guided through the optical fiber 11 is reflected by the return reflector 19, is guided through the same optical fiber 11 in the opposite direction, and enters the optical coupler 14.

(Light Receiver)

The light receiver 13 is optically connected to the proximal end of the optical fiber 11. The light receiver 13 receives light that is guided and returned through the optical fiber 11. Part of the light incident upon the optical coupler 14, e.g. 50% of light is guided toward the light receiver 13 and the remaining 50% of light is guided to the light source 12. The light guided toward the light receiver 13 is received by the light receiver 13. The light receiver 13 is a spectroscope capable of separating at least a plurality of characteristic absorption bands to detect an amount of light.

(Arrangement of Sensing Parts in Optical Fiber)

Next, a detection extent of a plurality of sensing parts will be described. By each of the sensing parts (FIG. 1 shows three sensing parts 15 in one optical fiber 11), a curve amount of the sensing part itself is detected. In actuality, however, only a sensing part (having a length of 5 mm in the longitudinal direction of the multipoint detection fiber sensor 1) is not curved due to the structure and/or material quality of the multipoint detection fiber sensor 1 itself and/or a member incorporating the multipoint detection fiber sensor 1. Since the multipoint detection fiber sensor 1 is curved in the longitudinal direction in a certain extent (e.g. 60 mm), it is considered that a curve of a sensing part is detected not only at a position of the sensing part but also in a certain extent (e.g. in a sensing part 15 having a length of 5 mm in the longitudinal direction, 30 mm in each of the longitudinal directions of the optical fiber 11 from the center of the sensing part 15 in its longitudinal direction, i.e., a total of 60 mm).

Hereinafter, an extent in which a curve could be detected by the multipoint detection fiber sensor 1 as a whole will be defined as an overall effective detection area A1 and an extent in which a curve could be detected by one sensing part will be defined as an individual effective detection area A2 (refer to FIG. 1). If the individual effective detection area A2 is set broadly, the number of sensing parts can be decreased, but it results in lower accuracy of curved-shape detection. To detect a curved shape with high accuracy, the individual effective detection area A2 needs to be set in an extent in which accuracy does not become a problem, and the number of sensing parts needs to increase.

To increase the number of sensing parts per optical fiber, it is required to provide different absorbers for generating characteristic absorption bands, the number of which is the same as that of sensing parts. The type of absorber has its limitation, as does the number of sensing parts that can be provided per optical fiber. If, furthermore, the number of sensing parts per optical fiber increases, the technical difficulty level will increase, for example, computations for obtaining a curve amount of each of the sensing parts will be complicated.

To increase the number of sensing parts, therefore, the overall effective detection area A1 is formed by a plurality of sensing parts of a plurality of optical fibers. In the present embodiment, three optical fibers 11, 21 and 31, which correspond to the first optical fiber 11 of the first sensor unit 10, the second optical fiber 21 of the second sensor unit 20 and the third optical fiber 31 of the third sensor unit 30, are arranged in the overall effective detection area A1. In other words, the overall effective detection area A1 is formed by arraying individual effective detection areas A2 of a plurality of sensing parts 15, 25 and 35 of the optical fibers 11, 21 and 31 in the longitudinal direction. The sensing parts 15 of the first optical fiber 11, the sensing parts 25 of the second optical fiber 21, and the sensing parts 35 of the third optical fiber 31 are arranged at different positions in the longitudinal direction.

In the present embodiment, the adjacent sensing parts in the longitudinal direction of the multipoint detection fiber sensor 1 are arranged at different optical fibers. As shown in FIG. 1, for example, a plurality of sensing parts are arranged repeatedly from the distal end of the multipoint detection fiber sensor 1 in the following sequence: the sensing parts 15 of the first optical fiber 11, the sensing parts 25 of the second optical fiber 21, and the sensing parts 35 of the third optical fiber 31, and the overall effective detection area A1 is formed by an array of individual effective detection areas A2 of the sensing parts 15, 25 and 35.

Using the multipoint detection fiber sensor 1 described above, the calculator, not shown, computes a curved shape of the multipoint detection fiber sensor 1 from the length of an individual effective detection area of each of the sensing parts and a curve amount of each of the sensing parts, which are given as advance information.

(Advantages)

According to the present embodiment, the overall effective detection area A1, which is an extent in which the multipoint detection fiber sensor 1 detects curve amounts in the longitudinal direction, is formed by the individual effective detection areas A2 of the sensing parts 15, 25 and 35 of the optical fibers 11, 21 and 31. Accordingly, a thin, multipoint detection fiber sensor 1 can be provided which is capable of decreasing the number of optical fibers and increasing the number of detection points to achieve curved-shape detection with high-accuracy.

Furthermore, since a plurality of sensing parts are arranged in the longitudinal direction at different positions of a plurality of optical fibers, curve amounts can be measured at a plurality of points in the longitudinal direction of the multipoint detection fiber sensor 1.

Moreover, in the present embodiment, adjacent sensing parts are arranged at different optical fibers in the overall effective detection area A1. Thus, a distance between sensing parts at one optical fiber becomes longer than when adjacent sensing parts are arranged continuously at the same optical fiber. It is necessary to fix the optical fiber 11 when laser processing is performed to remove the jacket 18 and cladding 17 of the optical fiber 11 to form the sensing parts 15. If, however, a distance between the sensing parts is short, the range of fixing becomes hard to secure and the difficulty level of manufacturing of the sensing parts increases. According to the present embodiment, since adjacent sensing parts are arranged at different optical fibers to lengthen a distance between sensing parts at one optical fiber, the range of fixing necessary for forming the sensing parts becomes easy to secure and it can decrease the difficulty level of manufacturing of the sensing parts.

It is also necessary to measure an amount of variation in light by curving the sensing parts one by one when the relationship between the amount of curve of each sensing part of the optical fiber and the amount of variation in guided light is acquired. If a distance between sensing parts at one optical fiber is short at this time, a sensing part other than a sensing part for measurement is also easily curved at the same time, and it could be difficult to curve one sensing part only. According to the present embodiment, since adjacent sensing parts are arranged at different optical fibers to lengthen a distance between sensing parts at one optical fiber, only one sensing part can easily be curved.

In the present embodiment, absorbers having characteristic absorption bands that cause mutual absorption are provided for their respective sensing parts formed on the same optical fiber. This structure has a degree of freedom in a way to give absorption spectra and materials, as compared with a structure in which a plurality of sensing parts cause no mutual absorption and a larger number of sensing parts can be provided for one optical fiber.

Furthermore, in the present embodiment, the return reflectors 19, 29 and 39 are provided at end portions different from the portions to which the optical couplers 14, 24 and 34 of the optical fibers 11, 21 and 31 are connected; thus, light guided from the light sources is returned to the same optical fibers 11, 21 and 31 and guided to the light receivers 13, 23 and 33. In other words, light supplied from the light sources 12, 22 and 32 and entering the reflectors 19, 29 and 39 and light received by the light receivers 13, 23 and 33 via the reflectors 19, 29 and 39 coexist in the same optical fibers 11, 21 and 31. Therefore, a thin multipoint detection fiber sensor 1 can be achieved by optical fibers the number of which is smaller than that of optical fibers through which light is guided from the light sources to the light receivers.

In the foregoing descriptions, the adjacent sensing parts 15, 25 and 35 in the longitudinal direction of the multipoint detection fiber sensor 1 are arranged at different optical fibers. However, as shown in FIG. 6, the adjacent sensing parts can be formed at one (the same) optical fiber.

Figure 6:
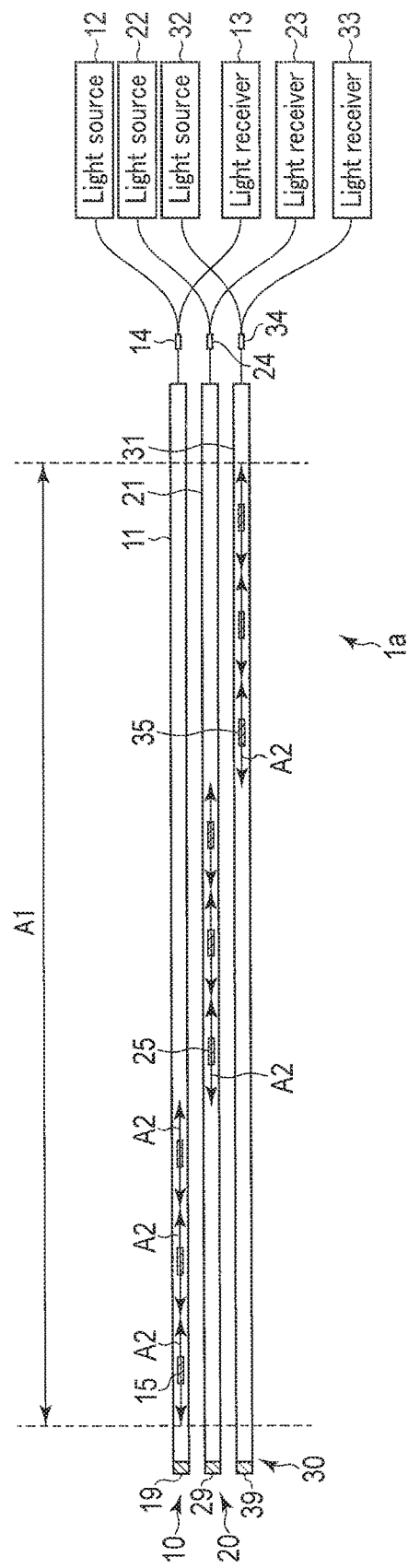
FIG. 6 is a diagram showing the overall structure of another multipoint detection fiber sensor according to the first embodiment.

FIG. 6 is a diagram showing the overall structure of another multipoint detection fiber sensor 1a according to the first embodiment. A plurality of sensing parts are arranged from the distal end of the multipoint detection fiber sensor 1 in the following sequence: three sensing parts 15 of the first optical fiber 11, three sensing parts 25 of the second optical fiber 21, and three sensing parts 35 of the third optical fiber 31, thereby forming an overall effective detection area A1.

Even in the above structure, curve amounts can be measured at a plurality of points in the longitudinal direction of the multipoint detection fiber sensor 1a.

In the foregoing descriptions, the direction of curve is a one direction. However, a multipoint detection fiber sensor is able to detect a two-direction curve by providing two sensing parts at the same positions in the longitudinal direction of the multipoint detection fiber sensor and at different positions in the radial direction.

Figure 7:
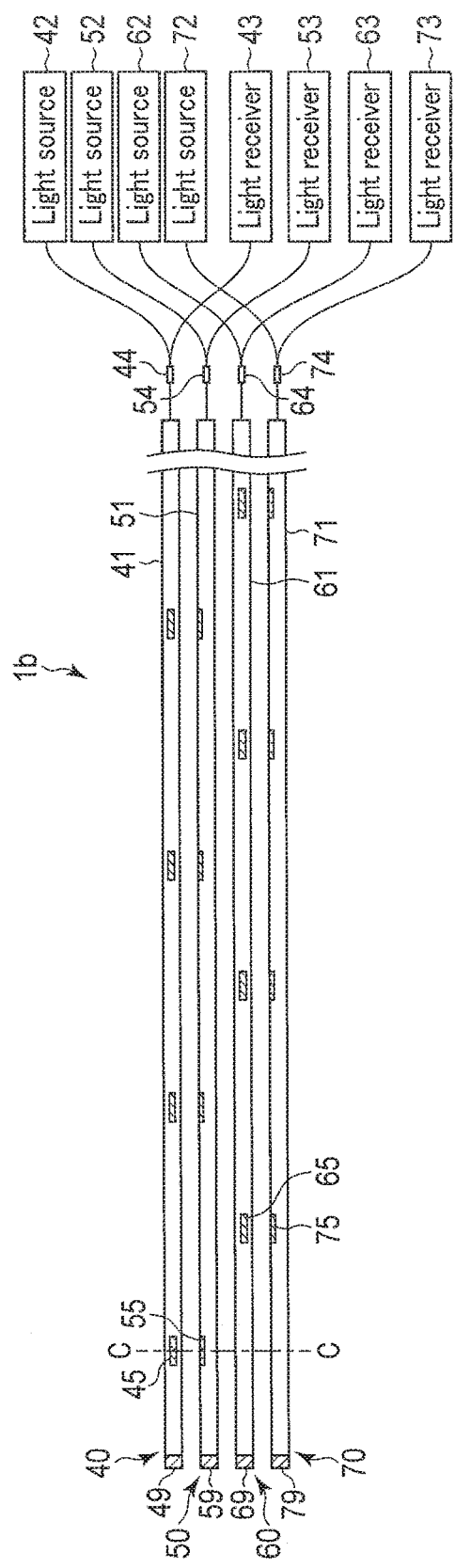
FIG. 7 is a diagram showing the overall structure of still another multipoint detection fiber sensor according to the first embodiment.

FIG. 7 is a diagram showing the overall structure of still another multipoint detection fiber sensor 1b according to the first embodiment. FIGS. 8a to 8d are sectional views taken along the line C-C of FIG. 7. The multipoint detection fiber sensor 1b detects a curve amount in each of an X axis direction and a Y axis direction orthogonal to the X axis direction by providing two sensing parts in the X axis and Y axis directions at the same positions in the longitudinal direction of the multipoint detection fiber sensor 1b.

The multipoint detection fiber sensor 1b includes a first sensor unit 40, a second sensor unit 50, a third sensor unit 60 and a fourth sensor unit 70. The first sensor unit 40 includes a first optical fiber 41, a light source 42 that supplies light to the first optical fiber 41, a light receiver 43 that receives light from the first optical fiber 41, and an optical coupler 44 that connects the first optical fiber 41 and the light source 42 and connects the first optical fiber 41 and the light receiver 43. Similarly, the second, third and fourth sensor units 50, 60 and 70 respectively include second, third and fourth optical fibers 51, 61 and 71, light sources 52, 62 and 72 that supply light to the respective optical fibers, light receivers 53, 63 and 73 that receive light from their respective optical fibers, and optical couplers 54, 64 and 74 that connect their respective optical fibers and light sources and connect their respective optical fibers and light receivers. The optical fibers 41, 51, 61 and 71 are provided with return reflectors 49, 59, 69 and 79 at their end portions. The optical fibers 41, 51, 61 and 71 respectively include cores 46, 56, 66 and 76, claddings 47, 57, 67 and 77 that surround the cores 46, 56, 66 and 76, and jackets 48, 58, 68 and 78 that surround the claddings 47, 57, 67 and 77.

Figure 8A:
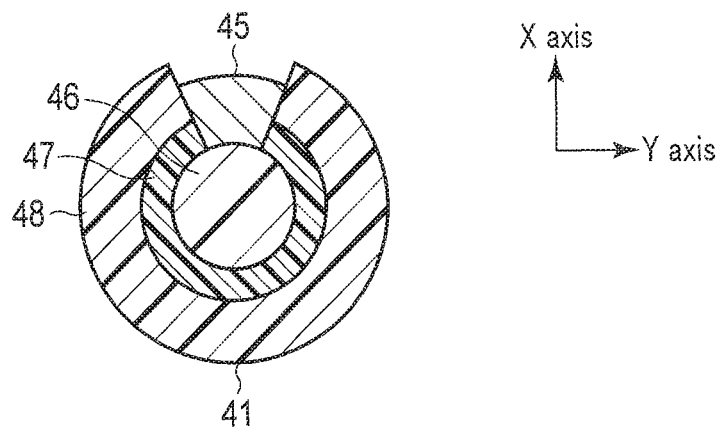
FIG. 8a is a sectional view of the first optical fiber, taken along the line C-C of FIG. 7.
Figure 8B:
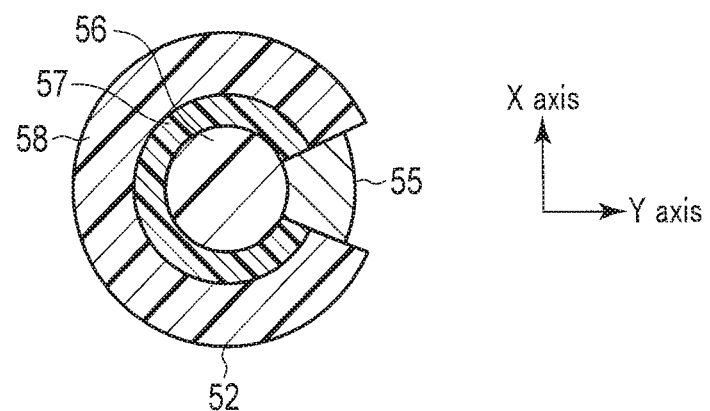
FIG. 8b is a sectional view of a second optical fiber, taken along the line C-C of FIG. 7.
Figure 8C:
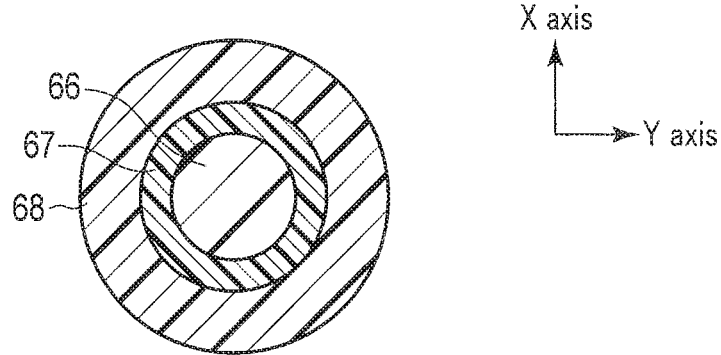
FIG. 8c is a sectional view of a third optical fiber, taken along the line C-C of FIG. 7.
Figure 8D:
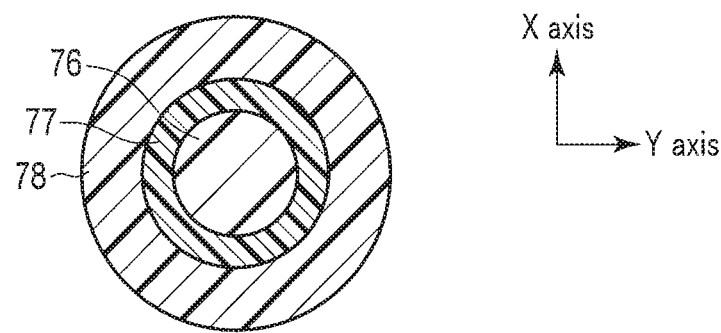
FIG. 8d is a sectional view of a fourth optical fiber, taken along the line C-C of FIG. 7.

The first optical fiber 41 is provided with a plurality of sensing parts 45. The sensing parts 45 are formed in a direction in which an X axis direction curve is detected, in the same manner as the sensing parts 15. The second optical fiber 15 is also provided with a plurality of sensing parts 55. The sensing parts 55 are also formed in a direction in which a Y axis direction curve is detected. As shown in FIGS. 8a and 8b, the sensing parts 45 and 55 are arranged at the same positions in the longitudinal direction of the multipoint detection fiber sensor 1b and displaced 90 degrees in the radial direction. Thus, the first optical fiber 41 and the second optical fiber 51 are paired optical fibers (hereinafter referred to as a first optical fiber pair), and the sensing parts 45 and 55 (hereinafter referred to as a first sensing part pair) are provided at the same positions in the longitudinal direction and at different positions in the radial direction.

Similarly, the third optical fiber 61 is provided with a plurality of sensing parts 65. The sensing parts 65 are also formed in a direction in which an X axis direction curve is detected. The fourth optical fiber 71 is also provided with a plurality of sensing parts 75. The sensing parts 75 are formed in a direction in which a Y axis direction curve is detected. Like the sensing parts 45 and 55, the sensing parts 65 and 75 are arranged at the same positions in the longitudinal direction of the multipoint detection fiber sensor 1b and displaced 90 degrees in the radial direction. The third optical fiber 61 and the fourth optical fiber 71 are also paired optical fibers (hereinafter referred to as a second optical fiber pair), and the sensing parts 65 and 75 (hereinafter referred to as a second sensing part pair) are provided at the same positions in the longitudinal direction and at different positions in the radial direction.

As shown in FIG. 7, the first sensing part pairs and the second sensing part pairs are arranged at different positions in the longitudinal direction of the multipoint detection fiber sensor 1b. Furthermore, adjacent sensing part pairs in the longitudinal direction of the multipoint detection fiber sensor 1b are arranged at different optical fiber pairs. As shown in FIG. 7, for example, the sensing parts are repeatedly arranged from the distal end of the multipoint detection fiber sensor 1b in the following sequence: the first sensing part pair and the second sensing part pair, thereby forming an overall effective detection area A1 not shown.

According to the structure of the multipoint detection fiber sensor 1b, the sensing part pairs are provided in the X axis direction and the Y axis direction orthogonal to the X axis direction, with the result that a curve amount can be detected in each of the directions.

The angle between the directions of sensing parts of each sensing part pair is not limited to 90 degrees but has only to be one excluding 180 degrees. However, it is preferable that the angle is closer to 90 degrees because the separation precision is likely to lower when the angle is close to 0 degree and 180 degrees.

[Variants]

Below are descriptions of a variant to the first embodiment. In the following descriptions, the same structural elements as those of the first embodiment are denoted by the same reference numerals as those of the first embodiment and their detailed descriptions are omitted.

FIG. 9 is a diagram showing the overall structure of a multipoint detection fiber sensor 1c according to variant 1. The multipoint detection fiber sensor 1c includes a first sensor unit 40c and a second sensor unit 60c.

The first sensor unit 40c includes a first optical fiber 41c, a second optical fiber 51c, a light source 42 that supplies light to the first optical fiber 41c, and a light receiver 53 that receives light emitted through the second optical fiber 51c. Similarly, the second sensor unit 60c includes a third optical fiber 61c and a fourth optical fiber 71c, a light source 62 that supplies light to the third optical fiber 61c, and a light receiver 73 that receives light emitted through the fourth optical fiber 71c.

The first optical fiber 41c, second optical fiber 51c, third optical fiber 61c and fourth optical fiber 71c are provided with a plurality of sensing parts 45c, a plurality of sensing parts 55c, a plurality of sensing parts 65c and a plurality of sensing parts 75c, respectively, in the same manner as in the first embodiment. These sensing parts 45c, 55c, 65c and 75c are arranged at different positions in the longitudinal direction to form an overall effective detection area A1 of the multipoint detection fiber sensor 1c. Adjacent sensing parts in the longitudinal direction of the multipoint detection fiber sensor 1c are arranged at different optical fibers. As shown in FIG. 9, for example, a plurality of sensing parts are arranged repeatedly from the distal end of the multipoint detection fiber sensor 1c in the following sequence: the sensing parts 45c of the first optical fiber 41c, the sensing parts 55c of the second optical fiber 51c, the sensing parts 65c of the third optical fiber 61c, and the sensing parts 75c of the fourth optical fiber 71c, thereby forming an overall effective detection area A1.

In the first sensor unit 40c, the distal end of the first optical fiber 41c and that of the second optical fiber 51c are optically connected through an optical connector. In this variant, the optical connector is an optical fiber 49c through which the first optical fiber 41c and the second optical fiber 51c are connected at other than the overall effective detection area A1. Thus, the first optical fiber 41c, second optical fiber 51c and optical fiber 49c for connection constitute a first optical fiber unit. Similarly, in the second sensor unit 60c, the distal end of the third optical fiber 61c and that of the fourth optical fiber 71c are optically connected to each other through an optical fiber 69c, which is an optical connector, at other than the overall effective detection area A1. The third optical fiber 61c, fourth optical fiber 71c and optical fiber 69c also constitute a second optical fiber unit.

The first optical fiber 41c and second optical fiber 51c are so configured that they are connected through the optical fiber 49c by fusion, or they are caused to turn back. The third optical fiber 61c and fourth optical fiber 71c are configured in a like manner.

As described above, in the first embodiment, light guided from a light source is guided to a light receiver through the same optical fiber, but another structure can be adopted if a plurality of optical fibers have only to be arranged at the overall effective detection area A1. In other words, as in the present variant, a plurality of optical fibers can be connected through an optical connector, and light traveling from a light source to an optical connector and light traveling from the optical connector to a light receiver may exist in different optical fibers in the overall effective detection area A1. One or some turning-back optical fibers (two in the overall effective detection area) can be provided for the multipoint detection fiber sensor 1c.

According to the present variant, no return reflector needs to be manufactured or no optical coupler is required. Therefore, the structure can be simplified.

Figure 10:
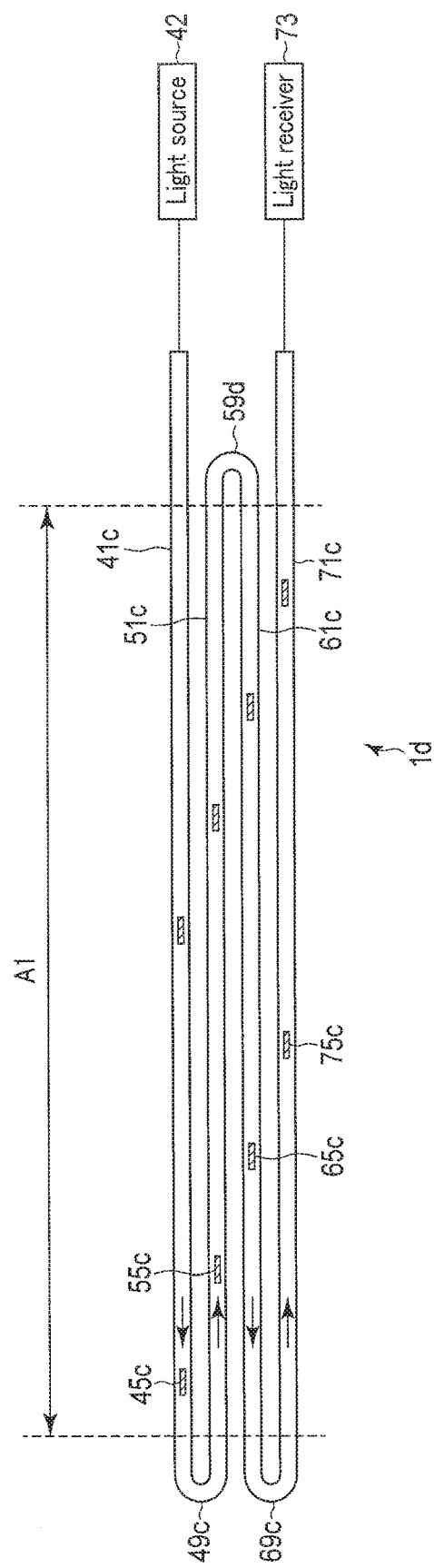
FIG. 10 is a diagram showing the overall structure of a multipoint detection fiber sensor according to variant 2 of the first embodiment.

FIG. 10 is a diagram showing the overall structure of a multipoint detection fiber sensor 1d according to variant 2. The multipoint detection fiber sensor 1d includes a first optical fiber 41c, a second optical fiber 51c, a third optical fiber 61c, a fourth optical fiber 71c, a light source 42 that supplies light to the first optical fiber 41c, and a light receiver 73 that receives light emitted through the fourth optical fiber 71c in the same manner as in variant 1. Sensing parts 45c, 55c, 65c and 75c are arranged in the optical fibers 41c, 51c, 61c and 71c in the same manner as in variant 1.

In the present variant, the distal end of the second optical fiber 51c and that of the third optical fiber 61c, as well as the optical fibers 49c and 69c that are the same optical connectors as in variant 1, are optically connected through an additional optical connector. The additional optical connector is an optical fiber 59d through which the second optical fiber 51c and the third optical fiber 61c are connected to each other at other than the overall effective detection area A1. With the optical fibers 49c, 59d and 69c serving as optical connectors, the multipoint detection fiber sensor 1d is so configured that one optical fiber is folded three times (a plurality of times).

In the present variant, too, no return reflector needs to be manufactured. Therefore, the structure can be simplified.

Figure 11:
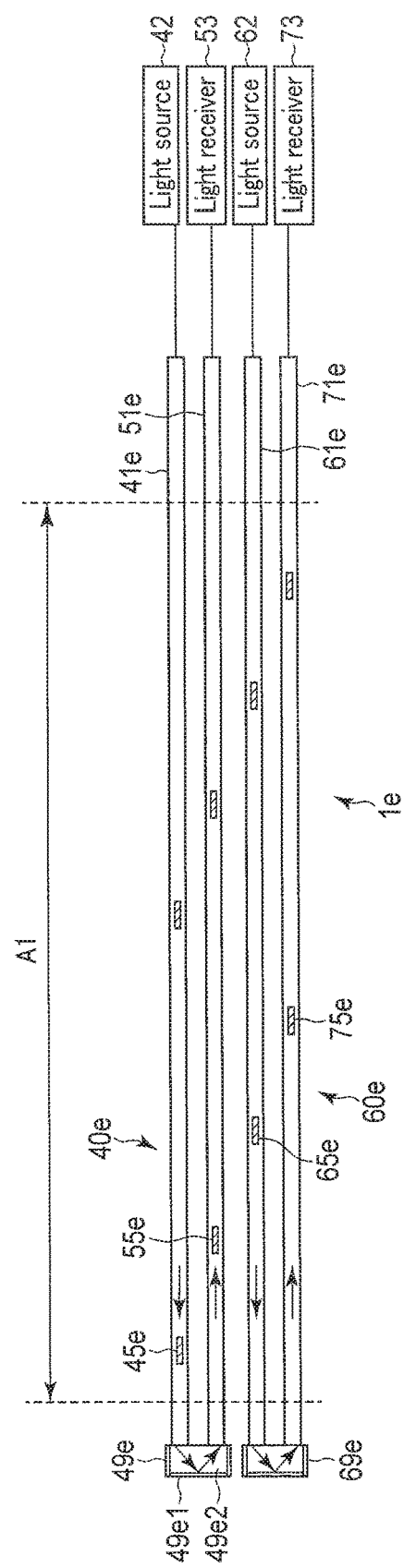
FIG. 11 is a diagram showing the overall structure of a multipoint detection fiber sensor according to variant 3 of the first embodiment.

FIG. 11 is a diagram showing the overall structure of a multipoint detection fiber sensor 1e according to variant 3. The multipoint detection fiber sensor 1e includes a first sensor unit 40e and a second sensor unit 60e. The first sensor unit 40e includes a first optical fiber 41e, a second optical fiber 51e, a light source 42 that supplies light to the first optical fiber 41e, and a light receiver 53 that receives light emitted through the second optical fiber 51e in the same manner as in variant 1. Similarly, the second sensor unit 60e includes a third optical fiber 61e, a fourth optical fiber 71e, a light source 62 that supplies light to the third optical fiber 61e, and a light receiver 73 that receives light emitted through the fourth optical fiber 71e. Sensing parts 45e, 55e, 65e and 75e are arranged in the optical fibers 41e, 51e, 61e and 71e in the same manner as in variant 1.

In the present variant, optical connecting reflectors 49e and 69e are provided as optical connectors in place of the optical fibers 49c and 69c of variant 1. More specifically, the optical connectors are optical connecting reflectors 49e and 69e through which the first optical fiber 41e and second optical fiber 51e are optically connected and the third optical fiber 61e and fourth optical fiber 71e are optically connected at other than the overall effective detection area A1. For example, the optical connecting reflectors 49e and 69e are formed by sticking aluminum 49e2, which is a reflection member, on glass 49e1 that is a transparent member. Thus, the first optical fiber 41e, second optical fiber 51e and optical connecting reflector 49e constitute a first optical fiber unit. Furthermore, the third optical fiber 61e, fourth optical fiber 71e and optical connecting reflector 69e constitute a second optical fiber unit.

When optical connectors are provided such that the optical fibers are folded as invariants 1 and 2, there is a case where the folded portions will be large due to limitations on the minimum bend radius of the optical fibers. In the present variant, however, the optical connectors are optical connecting reflectors 49e and 69e, which subject no limitation on the bend radius of the optical fibers. Therefore, light can be guided from the first optical fiber 41e to the second optical fiber 51e and from the third optical fiber 61e to the fourth optical fiber 71e without making the folded portions large.

Figure 13A:
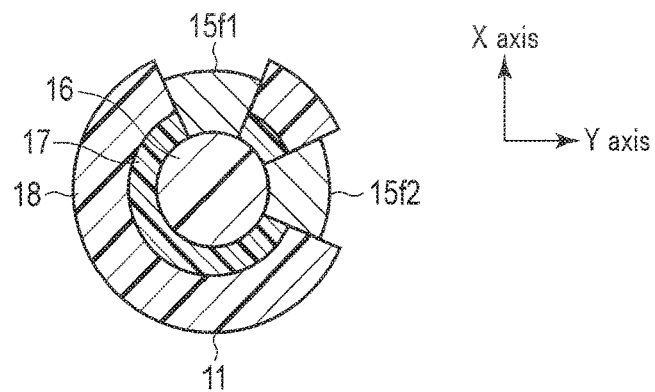
FIG. 13a is a sectional view of the first optical fiber, taken along the line D-D of FIG. 12.
Figure 13B:
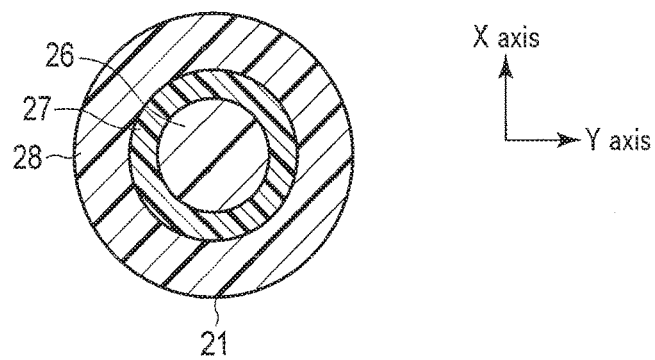
FIG. 13b is a sectional view of the second optical fiber, taken along the line D-D of FIG. 12.
Figure 13C:
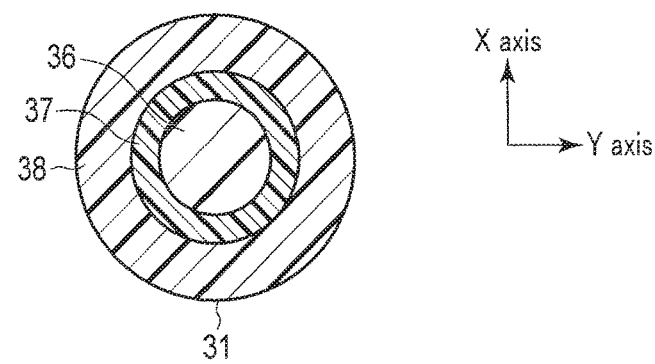
FIG. 13c is a sectional view of the third optical fiber, taken along the line D-D of FIG. 12.

FIG. 12 is a diagram showing the overall structure of a multipoint detection fiber sensor 1f according to variant 4. FIGS. 13a to 13c are sectional views, taken along the line D-D of FIG. 12. The multipoint detection fiber sensor 1f includes a first sensor unit 10f, a second sensor unit 20f and a third sensor unit 30f.

The first sensor unit 10f includes a first optical fiber 11f, a light source 12 that supplies light to the first optical fiber 11f, a light receiver 13 that receives light emitted through the first optical fiber 11f, an optical coupler 14 through which the first optical fiber 11f and the light source 12 are connected and the first optical fiber 11f and the light receiver 13 are connected. Likewise, the second sensor unit 20f and the third sensor unit 30f respectively include a second optical fiber 21f and a third optical fiber 31f, light sources 22 and 32 that supply light to their respective second and third optical fibers 21f and 31f, light receivers 23 and 33 that receive light emitted through their respective second and third optical fibers 21f and 31f, and optical couplers 24 and 34 through which the respective optical fibers and light sources are connected and the respective optical fibers and light receivers are connected. Furthermore, as in the first embodiment, return reflectors 19, 29 and 39 are provided at the distal ends of the optical fibers 11f, 21f and 31f, respectively.

According to the present variant, in the first optical fiber 11f, a sensing part 15f1 for detecting an X axis direction curve and a sensing part 15f2 for detecting a Y axis direction curve are arranged at the same positions in the longitudinal direction and displaced 90 degrees in the radial direction. These sensing parts 15f1 and 15f2 constitute a sensing part pair 15f. The first optical fiber 11f includes a plurality of sensing part pairs 15f. Similarly, the second optical fiber 21f and third optical fiber 31f respectively include a plurality of sensing part pairs 25f each having a sensing part 25f1 and a sensing part 25f2 and a plurality of sensing part pairs 35f each having a sensing part 35f1 and a sensing part 35f2. As shown in FIG. 12, for example, the sensing part pairs are arranged repeatedly from the distal end of the multipoint detection fiber sensor if in the following sequence: the sensing part pairs 15f of the first optical fiber 11f, the sensing part pairs 25f of the second optical fiber 21f, and the sensing part pairs 35f of the third optical fiber 32f, thereby forming an overall effective detection area A1 not shown.

When a multipoint detection fiber sensor detects both an X axis direction curve and a Y axis direction curve, if one sensing part of a sensing part pair and the other sensing part thereof are formed at different optical fibers, it is necessary to assemble the multipoint detection fiber sensor by combining the optical fibers while matching relative detection-direction angles of the sensing part pair at the time of manufacturing. Then, the width of each sensing part is small (e.g. several tens of micrometers); thus, the multipoint detection sensor has to be assembled by matching the directions using a microscope, which takes a lot of trouble.

Thus, the sensing parts in the respective directions can be provided at the same optical fiber as a sensing part pair, as in the present variant. Since, therefore, a relative angle between the X axis direction sensing part and the Y axis direction sensing part is unchanged, the multipoint detection sensor 1f can be assembled without concern for the rotation direction.

FIG. 14 is a diagram showing the overall structure of a multipoint detection fiber sensor 1g according to variant 5. The multipoint detection fiber sensor 1g includes a first sensor unit 10g, a second sensor unit 20g and a third sensor unit 30g. The first sensor unit 10g is configured in the same manner as the first sensor unit 10 of the first embodiment. The second sensor unit 20g and third sensor unit 30g are also configured in the same manner as the second sensor unit 20 and third sensor unit 30 of the first embodiment, respectively.

In the present variant, a distance between the distal end of the optical fiber 11 and a distal-end sensing part 15g1, which is a sensing part nearest to the distal end, is L1. The length between the distal end of the optical fiber 21 and a distal-end sensing part 25g1, which is a sensing part nearest to the distal end, and a distance between the distal end of the optical fiber 31 and a distal-end sensing part 35g1, which is a sensing part nearest to the distal end, are each L1 and the same. L1 is set to such a length as not to prevent the distal-end sensing parts 15g1, 25g1 and 35g1 from being curved, and it is, for example, 5 to 50 mm.

Furthermore, in the present variant, the distal end of the second optical fiber 21 is displaced from the distal end of the first optical fiber 11 to the proximal end thereof, and the distal end of the third optical fiber 31 is displaced from the distal end of the second optical fiber 21 to the proximal end thereof. Thus, the positions of the distal ends of the optical fibers 11, 21 and 31 differ from one another in the longitudinal direction, and the number of optical fibers at the distal end of the multipoint detection fiber sensor 1g decreases.

There is a case where an end portion of an optical fiber on the return reflector side, or a portion close to the distal end is hard to curve smoothly and does not extend along the multipoint detection fiber sensor. If, therefore, there is a sensing part close to the distal end of an optical fiber, curve amounts cannot be detected with high accuracy. Thus, in the present variant, a distance L1 between the distal end of the optical fiber 11 and the distal-end sensing part 15g1, which is a detected section nearest to the distal end, is set to such a length as not to prevent the distal-end sensing part 15g1 from being curved. Furthermore, the length L1 from the distal end of the optical fiber to the distal-end sensing part 15g1 is set not longer than necessary.

The length L1 is, for example, 5 mm to 50 mm. The detection accuracy of curve amounts varies with how to use a fiber sensor. When high detection accuracy is not required, it does not matter that L1 is short like 5 mm. On the other hand, when high detection accuracy is required, it is preferable that L1 is long like 50 mm. Accordingly, the number of optical fibers is decreased at a position closer to the distal end of the multipoint detection fiber sensor 1g with accuracy required for the distal-end sensing part 15g1; thus, space for arrangement of the optical fibers can be lessened.

There is a case where ease of curve varies with position and direction among objects to be detected by the multipoint detection fiber sensor 1g due to its structure and material. When the distal-end sensing part 15g1 is provided at a position where it is hard to curve, trackability required for curve of an object becomes low and thus it does not matter that the length L1 is short like 5 mm. On the other hand, when the distal-end sensing part 15g1 is provided at a position where it is easy to curve, trackability required for curve of an object becomes high and thus it is preferable that the length L1 is long like 50 mm.

Furthermore, ease of curve varies with thickness and material of an optical fiber. If the optical fiber is thin and made of soft material, for example, if its diameter is 200 μm and its core and cladding are made of resin, the length L1 may be short like 5 mm. On the other hand, if the optical fiber is thick and made of hard material, for example, if its diameter is 500 μm and its core and cladding are made of glass, it is preferable that the length L1 is long like 50 mm.

Moreover, if the distal-end sensing parts 15g1, 25g1 and 35g1 are too close to the distal ends of the optical fibers 11, 21 and 31 when the return reflectors 19, 29 and 39 are formed at the distal ends, the distal-end sensing parts 15g1, 25g1 and 35g1 are easily damaged, and the difficulty level of manufacturing of the multipoint detection fiber sensor increases. Accordingly, when the length L is 5 mm or longer, preferably 15 mm or longer, the difficulty level of manufacturing decreases.

Figure 15:
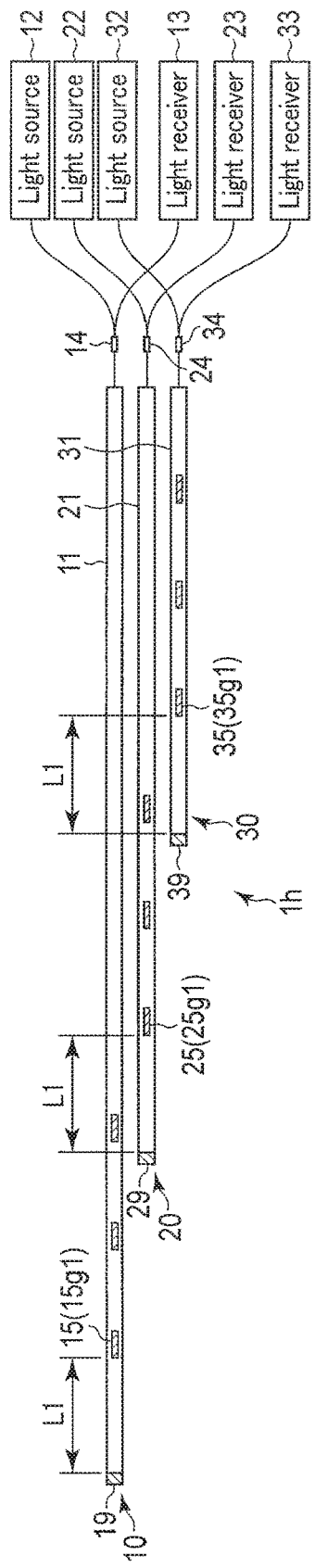
FIG. 15 is a diagram showing the overall structure of a multipoint detection fiber sensor according to variant 6 of the first embodiment.

FIG. 15 is a diagram showing the overall structure of a multipoint detection fiber sensor 1h according to variant 6. Like in the first embodiment shown in FIG. 6, in the present variant, a plurality of sensing parts are arranged from the distal end of the multipoint detection fiber sensor 1h in the following sequence: three sensing parts 15 of the first optical fiber 11, three sensing parts 25 of the second optical fiber 21 and three sensing parts 35 of the third optical fiber 31.

In variant 5, adjacent sensing parts in the longitudinal direction of the multipoint detection fiber sensor 1g are arranged at different optical fibers; however, as in variant 6, adjacent sensing parts in the longitudinal direction of the multipoint detection fiber sensor 1h can be formed at a single optical fiber. Even in this structure, curve amounts can be measured at a plurality of points in the longitudinal direction of the multipoint detection fiber sensor 1h.

In the present variant, a distance between the distal end of the optical fiber 11 and the distal-end sensing part 15g1, which is a sensing part nearest to the distal end, is also L1. A distance between the distal end of the optical fiber 21 and the distal-end sensing part 25g1, which is a sensing part nearest to the distal end, and the length between the distal end of the optical fiber 31 and the distal-end sensing part 35g1, which is a sensing part nearest to the distal end, are also each L1. Furthermore, in the present variant, too, the number of optical fibers at the distal end of the multipoint detection fiber sensor 1h is small.

According to the present variant, space necessary for arrangement of the optical fibers can be lessened while securing accuracy required for the distal-end sensing parts, as in variant 5.

FIG. 16 is a diagram showing the overall structure of a multipoint detection fiber sensor 1i according to variant 7. The multipoint detection fiber sensor 1i includes a first sensor unit 40i and a second sensor unit 60i. The first sensor unit 40i and second sensor unit 60i are configured in the same manner as the first sensor unit 40c and second sensor unit 60c of variant 1 shown in FIG. 9. Furthermore, a distance between the distal end of the optical fiber 49c that is an optical connector and a distal-end sensing part 45c1 that is a sensing part nearest to the distal end, is L2. A distance between the distal end of the optical fiber 69c and a distal-end sensing part 65c1 that is a sensing part nearest to the distal end, is also L2 and the same.

In the present variant, too, the length L2 from the optical connector to the distal-end sensing part that is nearest to the optical connector can be set to such a length as not to prevent the distal-end sensing part from being curved as in variant 5, and set not longer than necessary.

Figure 17:
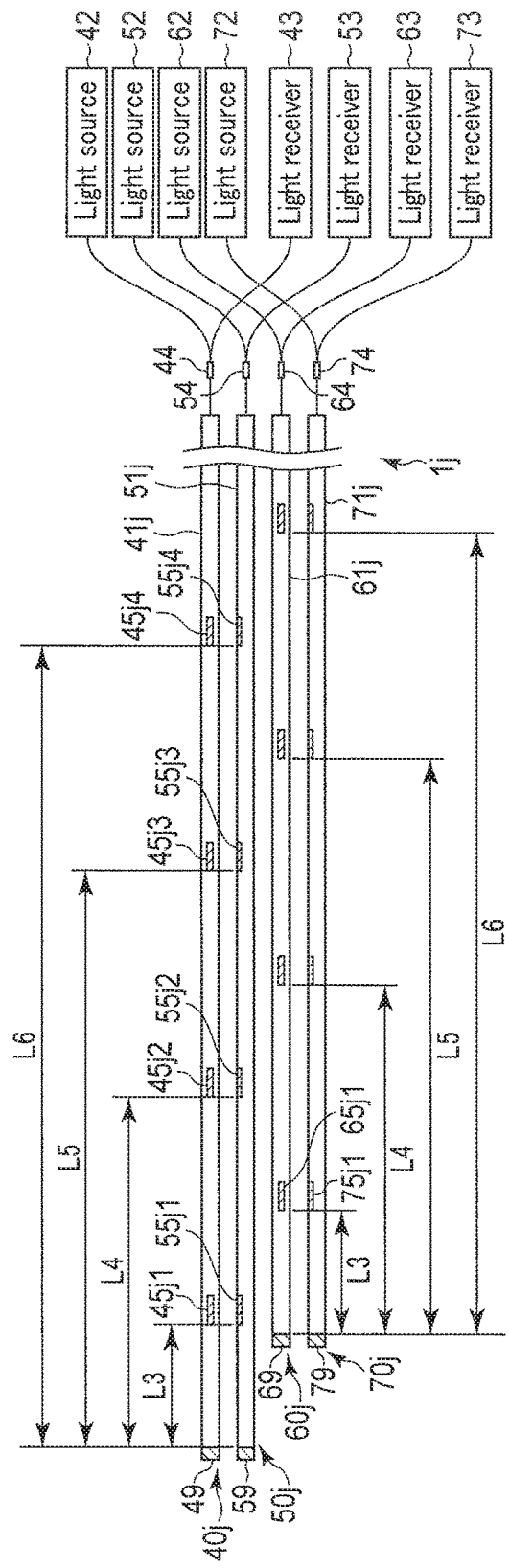
FIG. 17 is a diagram showing the overall structure of a multipoint detection fiber sensor according to variant 8 of the first embodiment.

FIG. 17 is a diagram showing the overall structure of a multipoint detection fiber sensor 1j according to variant 8. The multipoint detection fiber sensor 1j includes a first sensor unit 40j, a second sensor unit 50j, a third sensor unit 60j and a fourth sensor unit 70j as in the first embodiment shown in FIG. 7.

In the present variant, a distance between the distal end of the first optical fiber pair and a distal-end sensing part pair (sensing parts 45j1 and 55j1), which is a sensing part pair nearest to the distal end, is L3. Furthermore, a distance between the distal end of the first optical fiber pair and a distal-end sensing part pair (sensing parts 45j2 and 55j2), which is a sensing part pair nearer to the proximal end than the distal-end sensing part pair (sensing parts 45j1 and 55j1), is L4. Similarly, a distance between the distal end of the first optical fiber pair and a sensing part pair of sensing parts 45j3 and 55j3, which is nearer to the proximal end than the sensing part pair of sensing parts 45j2 and 55j2, is L5, and a distance between the distal end of the first optical fiber pair and a sensing part pair of sensing parts 45j4 and 55j4, which is nearer to the proximal end than the sensing part pair of sensing parts 45j3 and 55j3, is L6. Similarly, in the second optical fiber pair, too, a sensing part pair is provided with each of distances L3 to L6.

In the present variant, in all of the optical fibers, distances between the distal ends of the optical fibers and the sensing part pairs are the same. More specifically, in the present variant, a plurality of optical fibers in which the lengths L3 to L6 from the return reflectors to the sensing part pairs are the same, are manufactured, and these optical fibers are displaced in the longitudinal direction of the multipoint detection fiber sensor 1j or rotated on the rotation axis of the optical fibers. Thus, the optical fibers have only to be manufactured to have the same structure, with the result that they can be done through the same process and the manufacturing becomes easier than manufacturing of optical fibers having different structures.

When the optical fibers are displaced in the longitudinal direction, the proximal ends of the optical fibers are not aligned. If, therefore, the proximal-end portions of the optical fibers are lengthened in advance and cut when necessary, the proximal ends can be aligned.

FIG. 18 is a diagram showing the overall structure of a multipoint detection fiber sensor 1k according to variant 9. The multipoint detection fiber sensor 1k includes a first sensor unit 40k and a second sensor unit 60k.

The first sensor unit 40k includes a first optical fiber 41k, a second optical fiber 51k, a light source 42 that supplies light to the first optical fiber 41k, and a light receiver 53 that receives light emitted through the second optical fiber 51k. Similarly, the second sensor unit 60k includes a third optical fiber 61k, a fourth optical fiber 71k, a light source 62 that supplies light to the third optical fiber 61k, and a light receiver 73 that receives light emitted through the fourth optical fiber 71k.

The first optical fiber 41k is provided with a plurality of sensing parts 45k, which are formed in a direction in which an X axis direction curve is detected, in the same manner as the sensing parts 15. The second optical fiber 51k is also provided with a plurality of sensing parts 55k, which are formed likewise in a direction in which a Y axis direction curve is detected. The first optical fiber 41k and second optical fiber 51k are paired optical fibers (hereinafter referred to as a first optical fiber pair), and the sensing parts 45k and 55k (hereinafter referred to as a first sensing part pair) are provided at the same positions in the longitudinal direction and at different positions in the radial direction. Similarly, the third optical fiber 61k and fourth optical fiber 71k are paired optical fibers (hereinafter referred to as a second optical fiber pair), and the sensing parts 65k and 75k (hereinafter referred to as a second sensing part pair) are provided at the same positions in the longitudinal direction and at different positions in the radial direction.

In the first sensor unit 40k, the distal end of the first optical fiber 41k and that of the second optical fiber 51k are optically connected through the optical fiber 49k, which is an optical connector, at other than the overall effective detection area A1. Similarly, in the second sensor unit 60k, the distal end of the third optical fiber 61k and that of the fourth optical fiber 71k are optically connected through the optical fiber 69k, which is an optical connector, at other than the overall effective detection area A1.

The multipoint detection fiber sensor 1k according to the present variant can be regarded as a structure in which variants 1, 7 and 8 are combined, and bring about the advantages of these variants.

Second Embodiment

FIG. 19 is a diagram showing the overall structure of an insertion apparatus 100 according to a second embodiment. The insertion apparatus 100 is configured by incorporating one of the multipoint detection fiber sensors 1 to 1k according to the first embodiment into a flexible insertion section to be inserted into an insertion target, and it is an apparatus capable of detecting a shape of the insertion section. The insertion apparatus 100 is, for example, an endoscope and a catheter. In the present embodiment, it will be described that the insertion apparatus is an endoscope. Furthermore, hereinafter, it will be described as the insertion apparatus 100 into which the multipoint detection fiber sensor 1j in variant 8 shown in FIG. 17 is incorporated.

(Overview of Insertion Apparatus)

The insertion apparatus 100 includes an endoscope 110 into which a multipoint detection fiber sensor 1j is incorporated, an apparatus main body 120 connected to the endoscope 110, and a display 130 connected to the apparatus main body 120. The apparatus main body 120 includes light sources 42, 52, 62 and 72 that supply light to the multipoint detection fiber sensor 1j (FIG. 19 shows only light sources 42 and 72), light-receiving units 43, 53, 63 and 73 that receive light returned from the multipoint detection fiber sensor 1j (FIG. 19 shows only light-receiving units 43 and 73), and a calculator 121 that computes a curved shape of an insertion section 111 (described later) of the endoscope 110 on the basis of the amount of light received by the light-receiving units 43, 53, 63 and 73. The apparatus main body 120 also includes, for example, a control section (not shown) which controls a predetermined function of a peripheral device including the endoscope 110, which is connected to the apparatus main body 120.

(Endoscope)

The endoscope 110 includes a flexible insertion section 111 to be inserted into an insertion target 200, an operation section main body 112 coupled to the proximal end of the insertion section 111, a plurality of optical fibers 41j, 51j, 61j, and 71j of the multipoint detection fiber sensor 1j extending from the operation section main body 112, and a cord section 113 including an optical fiber 118 for illumination light and wiring 119 for an image sensor (see FIG. 20 describe later). The endoscope 110 is attachably and detachably connected to the apparatus main body 120 via the cord section 113 to communicate with the apparatus main body 120.

The insertion section 111 is an elongated tubular portion on the distal-end side of the endoscope. The insertion section 111 includes a bending portion 114 on its distal-end side and an elongated flexible tube portion 115 on its proximal-end side. Though not shown, the distal end of the insertion section 111 incorporates, for example, an observation optical system including an objective lens, the image sensor that forms an optical image from the observation optical system and converts it into an electrical signal, and an illumination optical system including an illumination lens. The bending portion 114 is curved in a desired direction if an operator manually operates an operation knob 116 disposed on the operation section main body 112. The flexible tube portion 115 is freely curved along the curved shape of the insertion target 200.

In the insertion section 111, at least an overall effective detection area A1 of the multipoint detection fiber sensor 1j is formed. FIG. 20 is a diagram showing the internal structure of the insertion section 111. The insertion section 111 incorporates internal components, such as a channel tube 117 through which a treatment tool passes, an optical fiber 118 for illumination light, and wiring 119 for the image sensor. A plurality of optical fibers 41j, 51j, 61j and 71j are fixed onto the outer surface of the channel tube 117 by an adhesive or the like. The internal components for fixing the optical fibers are not limited to the channel tube 117 but may be a member that has only to be displaced along the movement of the insertion section 111. For example, the optical fiber 118 for illumination light and the wiring 119 for the image sensor can be used as the internal components for fixing the optical fibers.

(Calculator)

The calculator 121 solves a numerical expression from the amount of variation in light in a plurality of characteristic wavelength bands, which is received by the light receivers 43, 53, 63 and 73 to obtain a curve amount of each of the sensing parts 45j1, 55j1, 65j1 and 75j1 (a curve amount of a sensing part pair of sensing parts 45j1 and 55j1 and a curve amount of a sensing part pair of sensing parts 65j1 and 75j1) from the relationship between a curve amount of each detected section acquired by beforehand measurement and the amount of variation in light. Since the position of each of the sensing parts 45j1, 55j1, 65j1 and 75j1 with respect to the insertion section 111 is known, a curved shape of the insertion section 111 is computed from the positional information of each sensing part and the curve amount thereof.

(Display)

The display 130 is attachably and detachably connected to the display main body 120. The display 130 displays an image in the insertion target 200 imaged by the endoscope 110 and/or a curved shape of the insertion section 111 computed by the calculator 121.

(Advantages)

According to the present embodiment, a multipoint detection fiber sensor is incorporated into an insertion apparatus, with the result that the number of optical fibers can be decreased and the number of points at which a curve amount of the insertion section is detected can be increased. In other words, high-accuracy curved-shape detection can be achieved while preventing the diameter of an insertion section from becoming large. If the diameter of an insertion section is small, the insertion apparatus can be inserted into an insertion target whose inside is narrow. Furthermore, since an operator of the insertion apparatus is able to operate the insertion apparatus while looking at a shape of an insertion section detected at high accuracy, the operability of the insertion apparatus is improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multipoint detection fiber sensor including a plurality of sensing parts at a plurality of positions, the sensing parts being able to detect curve amounts respectively, the multipoint detection fiber sensor comprising:
    a plurality of optical fibers arranged in an overall effective detection area that is an extent in which the multipoint detection fiber sensor detects curve amounts, each of the optical fibers including a plurality of sensing parts;
    a light source which supplies light to the optical fibers; and
    a light receiver which receives light emitted through the optical fibers to which light is supplied,
    wherein the optical fibers have light absorption characteristics whose absorption wavelength characteristics are respectively different in a predetermined wavelength region emitted from the light source,
    the light absorption characteristics include characteristic absorption bands, the number of the characteristic absorption bands being equal to or larger than that of the sensing parts, the characteristic absorption bands being wavelength ranges having different light absorption rates in the predetermined wavelength region;
    the supplied light from the light source includes wavelength components of the characteristic absorption bands; and
    the light receiver is configured to detect an amount of light of the characteristic absorption bands.

2. The multipoint detection fiber sensor according to claim 1, wherein the overall effective detection area is formed by arraying individual effective detection areas in a longitudinal direction of the optical fiber, each individual effective detection area being an extent in which each of the sensing parts detects a curve amount in the longitudinal direction.

3. The multipoint detection fiber sensor according to claim 2, wherein:
    each of the optical fibers has a distal end and a proximal end;
    each of the optical fibers includes a return reflector at the distal end;
    the light source and the light receiver are optically connected to the proximal end;
    in the overall effective detection area, light supplied from the light source and traveling to the return reflector and light received by the light receiver via the return reflector coexist in the same optical fiber.

4. The multipoint detection fiber sensor according to claim 3, wherein at least one of the optical fibers is configured so that a distance between the distal end and a distal-end sensing part is set to such a length as not to prevent the distal-end sensing part from being curved, the distal-end sensing part being one of the sensing parts nearest to the distal end.

5. The multipoint detection fiber sensor according to claim 4, wherein the length not to prevent the distal-end sensing part from being curved is 5 to 50 mm.

6. The multipoint detection fiber sensor according to claim 3, wherein:
    in all the optical fibers, distances between the distal end and each of the sensing parts is the same; and
    positions of distal ends of the optical fibers are different from one another in the longitudinal direction.

7. The multipoint detection fiber sensor according to claim 3, wherein:
    distances between the distal end and each of the sensing parts are the same in all of the optical fibers; and
    the sensing parts of an optical fiber pair including two of the optical fibers are located in the same positions in the longitudinal direction and at different positions in a radial direction.

8. The multipoint detection fiber sensor according to claim 2, wherein:
    each of the optical fibers has a distal end and a proximal end;
    the multipoint detection fiber sensor comprises one or more optical fiber units, each optical fiber unit including two of the optical fibers and an optical connector through which the distal ends of the two of the optical fibers are optically connected;
    the light source is optically connected to the proximal end of one optical fiber of the optical fiber units, and the light receiver is optically connected to the proximal end of another optical fiber of the optical fiber units; and
    in the overall effective detection area, light supplied from the light source and traveling to the optical connector and light received by the light receiver via the optical connector exist in different optical fibers of the optical fiber units.

9. The multipoint detection fiber sensor according to claim 8, wherein the optical connector comprises an optical connecting reflector through which the one optical fiber is optically connected to said another optical fiber by reflecting light guided through the one optical fiber.

10. The multipoint detection fiber sensor according to claim 8, wherein the optical connector comprises an optical fiber.

11. The multipoint detection fiber sensor according to claim 8, wherein the optical fiber units are configured so that a distance between a distal end of the optical connector and a distal-end sensing part is set to such a length as not to prevent the distal-end sensing part from being curved, the distal-end sensing part being a sensing part nearest to the optical connector.

12. The multipoint detection fiber sensor according to claim 11, wherein the length not to prevent the distal-end sensing part from being curved is 5 to 50 mm.

13. The multipoint detection fiber sensor according to claim 8, comprising a plurality of optical fiber units, wherein distances between a distal end of the optical connector and each of the sensing parts are the same in all of the optical fiber units, and positions of distal ends of the optical fiber units are different from one another in the longitudinal direction.

14. The multipoint detection fiber sensor according to claim 8, comprising a plurality of optical fiber units, wherein distances between a distal end of the optical connector and each of the sensing parts are the same in all of the optical fiber units, and the sensing parts of two optical fibers of the optical fiber units are located at the same positions in the longitudinal direction and at different positions in a radial direction.

15. The multipoint detection fiber sensor according to claim 1, wherein sensing parts located at the same positions in a longitudinal direction of the multipoint detection fiber sensor and at different positions in a radial direction thereof and/or adjacent sensing parts are arranged at different optical fibers of the plurality of optical fibers in the overall effective detection area.

16. The multipoint detection fiber sensor according to claim 1, wherein the sensing parts of each of the optical fibers are arranged at the same positions in a longitudinal direction of the optical fibers and at different positions in a radial direction thereof.

17. An insertion apparatus comprising:

a flexible insertion section inserted into an insertion target;

a plurality of sensing parts at a plurality of positions of the insertion section, the sensing parts being able to detect curve amounts respectively, the sensing parts being incorporated into a plurality of optical fibers arranged in an overall effective detection area that is a range in which the sensing parts detect curve amounts, each of the optical fibers including the sensing parts;

a light source that supplies light to the optical fibers; and a light receiver that receives light emitted through the optical fibers to which light is supplied;

wherein the optical fibers have light absorption characteristics whose absorption wavelength characteristics are respectively different in a predetermined wavelength region emitted from the light source, the light absorption characteristics include characteristic absorption bands, the number of the characteristic absorption bands being equal to or larger than that of the sensing parts, the characteristic absorption bands being wavelength ranges having different light absorption rates in the predetermined wavelength region;

the supplied light from the light source includes wavelength components of the characteristic absorption bands; and the light receiver is configured to detect an amount of light of the characteristic absorption bands.

* * * * *